US009362570B2

(12) United States Patent
Lund et al.

(10) Patent No.: US 9,362,570 B2
(45) Date of Patent: Jun. 7, 2016

(54) ELONGATE BATTERY FOR IMPLANTABLE MEDICAL DEVICE

(71) Applicant: Medtronic, Inc., Minneapolis, MN (US)

(72) Inventors: Jeffrey S. Lund, Forest Lake, MN (US); Steven J. May, Minnetonka, MN (US); Donald R. Merritt, Brooklyn Center, MN (US); Hailiang Zhao, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/512,509

(22) Filed: Oct. 13, 2014

(65) Prior Publication Data

US 2015/0030916 A1    Jan. 29, 2015

Related U.S. Application Data

(63) Continuation of application No. 12/549,572, filed on Aug. 28, 2009.

(60) Provisional application No. 61/182,343, filed on May 29, 2009.

(51) Int. Cl.
| | |
|---|---|
| *H01M 2/02* | (2006.01) |
| *H01M 6/14* | (2006.01) |
| *H01M 2/18* | (2006.01) |
| *A61N 1/36* | (2006.01) |
| *H01M 4/70* | (2006.01) |
| *A61N 1/378* | (2006.01) |
| *H01M 2/10* | (2006.01) |
| *H01M 2/30* | (2006.01) |
| *H01M 4/06* | (2006.01) |
| *H01M 4/133* | (2010.01) |
| *H01M 4/134* | (2010.01) |
| *H01M 4/38* | (2006.01) |
| *H01M 4/583* | (2010.01) |
| *H01M 4/587* | (2010.01) |
| *H01M 4/02* | (2006.01) |
| *A61N 1/05* | (2006.01) |
| *A61N 1/375* | (2006.01) |

(52) U.S. Cl.
CPC . *H01M 6/14* (2013.01); *A61N 1/36* (2013.01); *A61N 1/378* (2013.01); *A61N 1/3787* (2013.01); *H01M 2/0202* (2013.01); *H01M 2/022* (2013.01); *H01M 2/105* (2013.01); *H01M 2/18* (2013.01); *H01M 2/30* (2013.01); *H01M 4/06* (2013.01); *H01M 4/133* (2013.01); *H01M 4/134* (2013.01); *H01M 4/382* (2013.01); *H01M 4/587* (2013.01); *H01M 4/5835* (2013.01); *H01M 4/70* (2013.01); *A61N 1/056* (2013.01); *A61N 1/375* (2013.01); *H01M 2004/025* (2013.01); *H01M 2004/027* (2013.01); *H01M 2004/028* (2013.01); *H01M 2220/30* (2013.01)

(58) Field of Classification Search
None
See application file for complete search history.

(56) References Cited

U.S. PATENT DOCUMENTS

| | | |
|---|---|---|
| 3,943,936 A | 3/1976 | Rasor et al. |
| 4,035,909 A | 7/1977 | Dey |
| 4,117,212 A | 9/1978 | Mead et al. |
| 4,376,811 A | 3/1983 | Goebel |
| 4,731,305 A | 3/1988 | Goebel et al. |
| 5,306,581 A | 4/1994 | Taylor et al. |
| 5,776,632 A | 7/1998 | Honegger |
| 5,869,205 A | 2/1999 | Mick et al. |
| 6,132,896 A | 10/2000 | Sunderland et al. |
| 6,238,813 B1 | 5/2001 | Maile et al. |
| 6,607,843 B2 | 8/2003 | Ruth, II et al. |
| 7,070,881 B2 | 7/2006 | Kishiyama et al. |
| 7,128,765 B2 | 10/2006 | Paulot et al. |
| 7,291,186 B2 | 11/2007 | Zhang |
| 7,292,890 B2 | 11/2007 | Whitehurst et al. |
| 7,410,512 B2 | 8/2008 | Tsukamoto et al. |
| 7,640,061 B2 | 12/2009 | He et al. |
| 2001/0002300 A1 | 5/2001 | Tinker et al. |
| 2001/0028976 A1 | 10/2001 | Treger et al. |
| 2002/0183823 A1 | 12/2002 | Pappu |
| 2003/0091893 A1 | 5/2003 | Kishiyama et al. |
| 2004/0101746 A1 | 5/2004 | Ota et al. |
| 2004/0127952 A1 | 7/2004 | O'Phelan et al. |

(Continued)

FOREIGN PATENT DOCUMENTS

| | | |
|---|---|---|
| JP | 20022352790 | 12/2002 |
| WO | 9741608 | 11/1997 |
| WO | 0074166 A1 | 12/2000 |
| WO | 2007059386 | 5/2007 |
| WO | 2007127636 A2 | 11/2007 |

OTHER PUBLICATIONS (PCT/US2010/036145) PCT Notification of Transmittal of the International Search Report and the Written Opinion of the International Searching Authority, Mailed Sep. 10, 2010, 13 pages.

(Continued)

*Primary Examiner* — Ladan Mohaddes

(57) ABSTRACT

A battery assembly for a medical device includes an elongate cathode, an elongate anode, an electrolyte, and an elongate housing assembly encapsulating the cathode, the anode, and the electrolyte. The battery assembly also includes a first electrode exposed from and electrically insulated from the housing assembly. One of the anode and the cathode is electrically coupled to the first electrode, and the other of the anode and the cathode is electrically coupled to the housing assembly. Respective axes of the cathode and the anode are substantially parallel to an axis of the housing assembly, and the cathode and anode each include a flat portion that face each other.

10 Claims, 10 Drawing Sheets

(56) References Cited

U.S. PATENT DOCUMENTS

| | | |
|---|---|---|
| 2004/0185337 A1 | 9/2004 | Ishizaki |
| 2005/0021108 A1 | 1/2005 | Klosterman et al. |
| 2006/0085971 A1 | 4/2006 | Andrews et al. |
| 2006/0166078 A1* | 7/2006 | Chen et al. ................. 429/62 |
| 2006/0222942 A1 | 10/2006 | Zhao et al. |
| 2006/0241705 A1 | 10/2006 | Neumann et al. |
| 2006/0275659 A1 | 12/2006 | Kim et al. |
| 2007/0066997 A1 | 3/2007 | He et al. |
| 2007/0088396 A1 | 4/2007 | Jacobson |
| 2007/0150020 A1 | 6/2007 | Hokanson et al. |
| 2007/0154801 A1 | 7/2007 | Hyung et al. |
| 2007/0179552 A1 | 8/2007 | Dennis et al. |
| 2007/0179581 A1 | 8/2007 | Dennis et al. |
| 2007/0202401 A1 | 8/2007 | Viavattine |
| 2007/0247786 A1 | 10/2007 | Aamodt et al. |
| 2007/0259255 A1 | 11/2007 | Leysieffer et al. |
| 2007/0281213 A1 | 12/2007 | Pyszczek |
| 2008/0077219 A1 | 3/2008 | Williams et al. |
| 2008/0085449 A1 | 4/2008 | Pyszczek et al. |
| 2008/0103556 A1 | 5/2008 | Li et al. |
| 2008/0148554 A1 | 6/2008 | Merrill et al. |
| 2008/0167702 A1 | 7/2008 | Ransbury et al. |
| 2008/0187829 A1 | 8/2008 | Brand |

OTHER PUBLICATIONS

Takeuchi, "Design Evolution of Defibrillator Batteries", Battery Conference on Applications and Advances, 1991. Proceedings of the Sixth Annual, pp. 13-20, Retrieved from the internet: URL:http://ieeexplore.ieee.org/stamp/stamp.jsp?tp=&arnumber=761474 [retrieved on Aug. 25, 2010] the whole document.

(PCT/US2010/035612) PCT Notification of Transmittal of the International Search Report and the Written Opinion of the International Searching Authority, mailed Oct. 1, 2010, 19 pages.

(PCT/US2010/034189) PCT Notification of Transmittal of the International Search Report and the Written Opinion of the International Searching Authority, mailed Jul. 19, 2010, 11 pages.

(PCT/US2010/035596) PCT Notification of Transmittal of the International Search Report and the Written Opinion of the International Searching Authority, mailed Sep. 13, 2010, 12 pages.

(PCT/US2010/035590) PCT Notification of Transmittal of the International Search Report and the Written Opinion of the International Searching Authority, mailed Sep. 10, 2010, 10 pages.

U.S. Appl. No. 12/547,875, by Lund et al., filed Aug. 26, 2009.
U.S. Appl. No. 12/547,903 by Anderson et al., filed Aug. 26, 2009.
U.S. Appl. No. 12/548,234 by Lund et aL, filed Aug. 26, 2009.
U.S. Appl. No. 12/549,469 by Lund et al., filed Aug. 28, 2009.

* cited by examiner

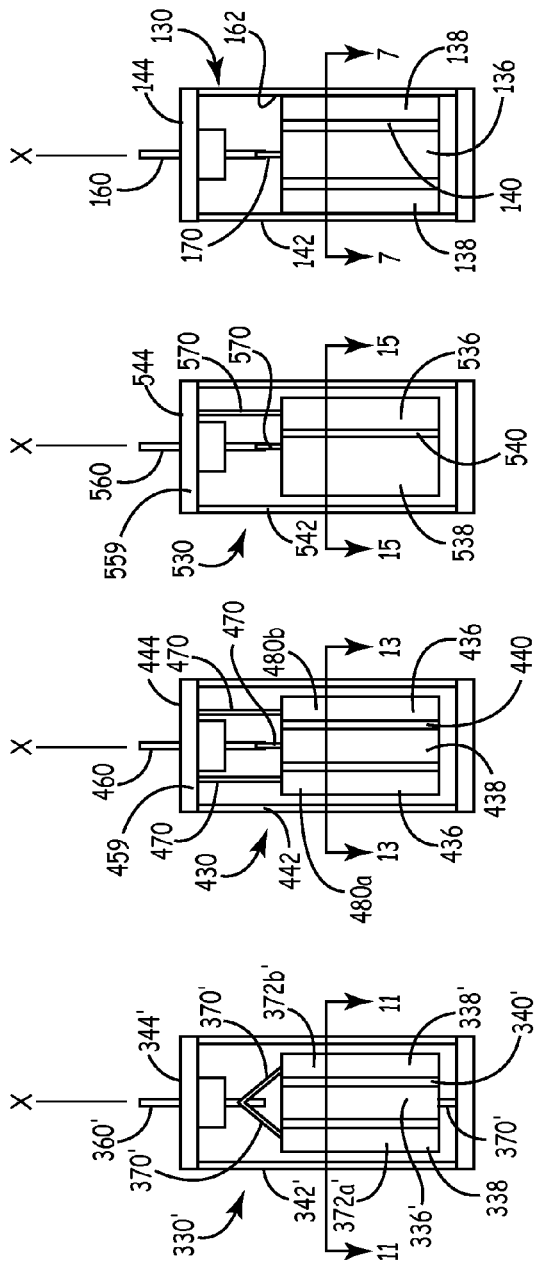

ELONGATE BATTERY FOR IMPLANTABLE MEDICAL DEVICE

CROSS-REFERENCE TO RELATED APPLICATIONS

This application is a continuation of U.S. patent application Ser. No. 12/549,572 filed on Aug. 28, 2009, which claims the benefit of U.S. Provisional Application No. 61/182,343, filed on May 29, 2009. The entire disclosure of the above application is incorporated herein by reference.

FIELD

The present disclosure relates to an implantable medical device, such as a cardiac pacemaker device, and in particular, an implantable medical device with an elongate battery.

INTRODUCTION

Several medical devices have been designed to be implanted within the human body. Implantable medical devices (IMDs), such as implantable pulse generators (IPGs), often include an elongate, flexible lead having one end operatively coupled to cardiac tissue and an opposite end operatively coupled to a generator (e.g., a pulse generator). The generator can include a power source, a sensing amplifier which processes electrical manifestations of naturally occurring heart beats as sensed by the lead, computer logic, and output circuitry, which delivers the pacing impulse to the cardiac tissue via the lead. Other IMDs, such as implantable cardioverter-defibrillators (ICDs), include similar components; however, these devices generate and deliver a defibrillation signal to the cardiac tissue via the respective lead.

The following discussion discloses a generator for an IMD that is very compact, such that generator can be readily implanted in small spaces within the patient's anatomy, and such that the generator is less likely to cause patient discomfort. Also, the generator can have a relatively high energy capacity to prolong the useful life of the device. Additionally, manufacturing of the IMD can be facilitated due to several features, which will be described in greater detail below.

SUMMARY

This section provides a general summary of the disclosure, and is not a comprehensive disclosure of its full scope or all of its features.

A battery assembly for a medical device is disclosed that includes an elongate cathode, an elongate anode, an electrolyte, and an elongate housing assembly encapsulating the cathode, the anode, and the electrolyte. The battery assembly also includes a first electrode exposed from and electrically insulated from the housing assembly. One of the anode and the cathode is electrically coupled to the first electrode, and the other of the anode and the cathode is electrically coupled to the housing assembly. Respective axes of the cathode and the anode are substantially parallel to an axis of the housing assembly, and the cathode and anode each include a flat portion that face each other.

In another aspect, a method of operatively coupling a medical device to a patient is disclosed. The method includes operatively coupling a lead of the medical device to cardiac tissue of the patient. The method also includes implanting a control assembly and a battery assembly of the medical device within the patient. The battery assembly includes a cathode, an anode, an electrolyte, a housing assembly encapsulating the cathode, the anode, and the electrolyte, and a first electrode exposed from and electrically insulated from the housing assembly. One of the anode and the cathode is electrically coupled to the first electrode, and the other of the anode and the cathode is electrically coupled to the housing assembly. Respective axes of the cathode and the anode are substantially parallel to an axis of the housing assembly, and the cathode and anode each include a flat portion that face each other. The method further includes supplying power from the battery assembly to the control assembly. Moreover, the method includes controlling electrical signal transmission through the pacing lead.

In still another aspect, a battery assembly for an implantable cardiac device is disclosed that is implantable in a biological tissue. The battery includes a D-shaped cathode, a D-shaped anode, an electrolyte, and a substantially cylindrical housing assembly encapsulating the cathode, the anode, and the electrolyte. The housing assembly, the cathode, and the anode each have a respective axis that are substantially parallel to each other. The battery assembly further includes a first electrode exposed from and electrically insulated from the housing assembly. One of the anode and the cathode is electrically coupled to the first electrode and the other of the anode and the cathode is electrically coupled to the housing assembly. The cathode and anode each include a flat portion that face each other.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is a section view of another exemplary embodiment of the battery assembly of the medical device;

FIG. 7 is a section view of the battery assembly of FIG. 6 taken along the line 7-7;

FIG. 10 is a section view of a portion of another exemplary embodiment of the battery assembly of the medical device;

FIG. 11 is a section view of the battery assembly of FIG. 10 taken along the line 11-11;

FIG. 12 is a section view of a portion of another exemplary embodiment of the battery assembly of the medical device;

FIG. 13 is a section view of the battery assembly of FIG. 12 taken along the line 13-13;

FIG. 14 is a section view of a portion of another exemplary embodiment of the battery assembly of the medical device;

FIG. 15 is a section view of the battery assembly of FIG. 14 taken along the line 15-15;

Corresponding reference numerals indicate corresponding parts throughout the several views of the drawings.

DETAILED DESCRIPTION

Exemplary embodiments will now be described more fully with reference to the accompanying drawings.

Figure 1:
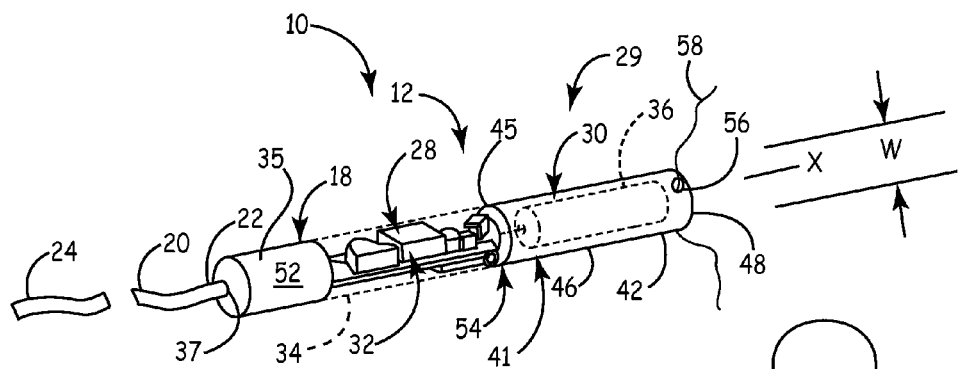
FIG. 1 is a perspective view of a medical device according to various teachings of the present disclosure.
Figure 2:
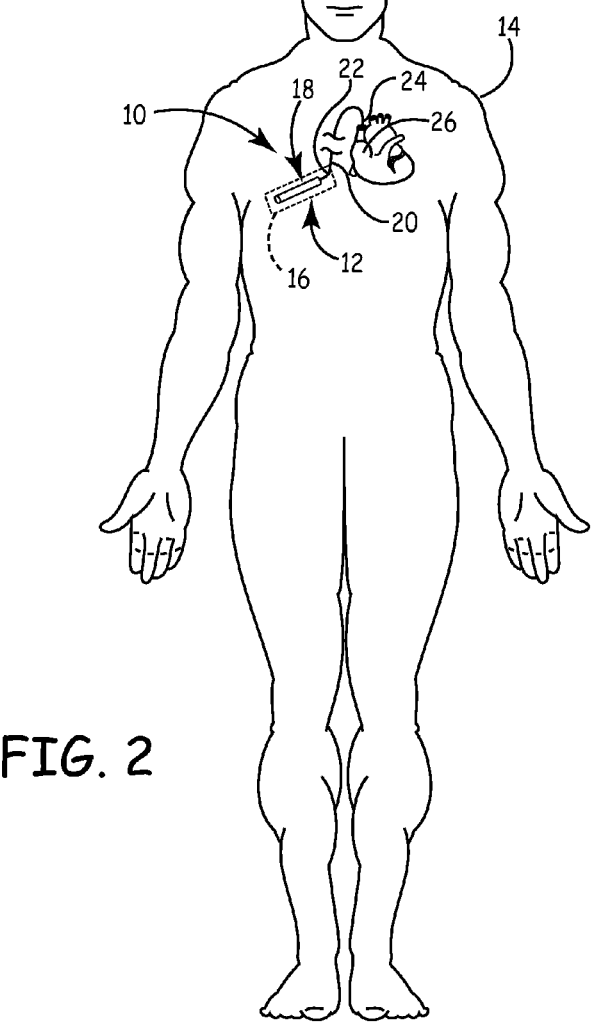
FIG. 2 is a schematic view of the medical device of FIG. 1 shown implanted within a patient.
Figure 3:
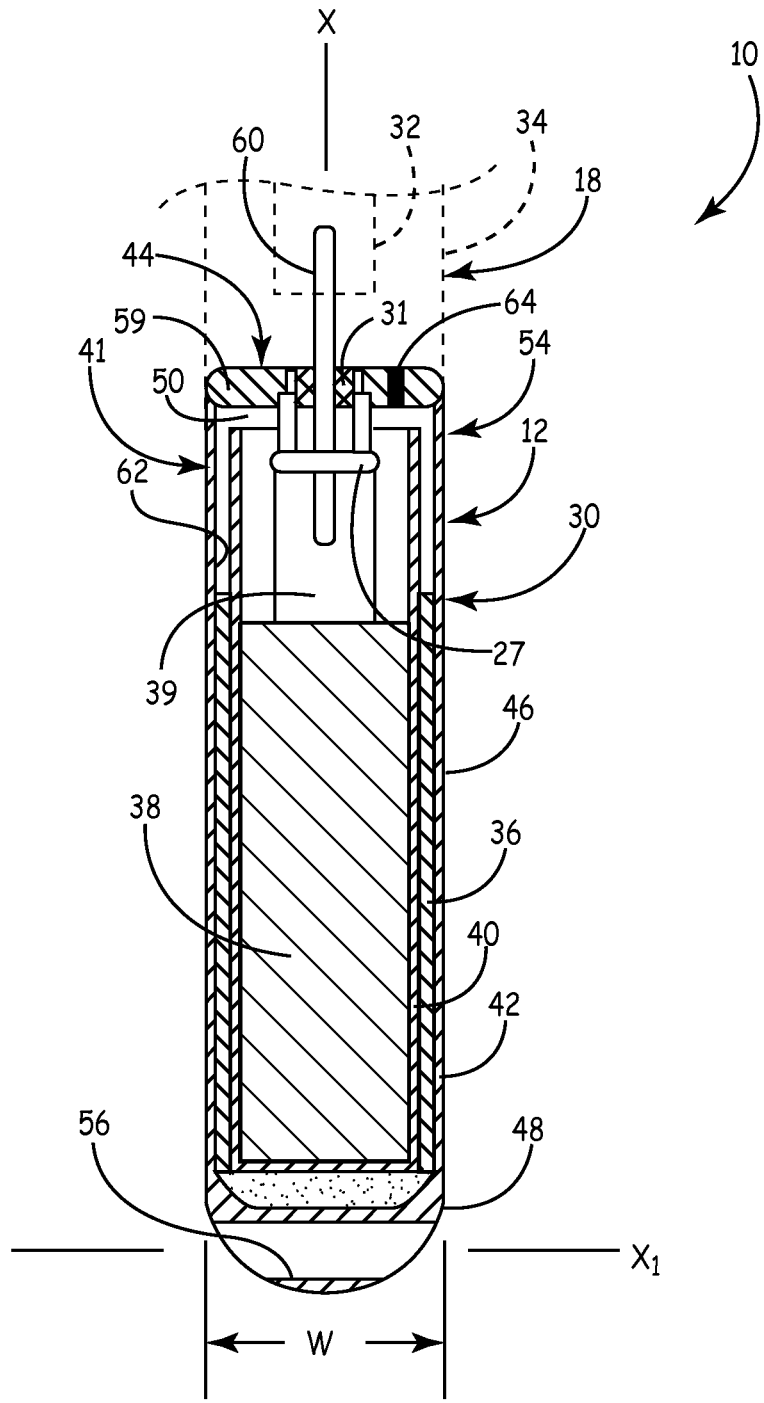
FIG. 3 is a partial section view of the medical device of FIG. 1.

Referring initially to FIGS. 1, 2, and 3, an implantable medical device 10 (IMD) is illustrated according to various teachings of the present disclosure. The medical device 10 can be of any suitable type, and in some embodiments, the medical device 10 can be a cardiac pacemaker device 12 (i.e., an implantable pulse generator). The cardiac pacemaker device 12 can be an electronic device for providing an electrical cardiac signal to stimulate cardiac tissue and to thereby maintain a predetermined heart beat as described in greater detail below. It will be appreciated, however, that the medical device 10 can be of any other suitable type, such as an implantable cardioverter-defibrillator (ICD), without departing from the scope of the present disclosure. In other embodiments, the medical device 10 can be a neural device for providing electrical signals to a nerve or for any other suitable neural application. In still other embodiments, the medical device 10 can be a pressure sensor (e.g., for measuring blood pressure). Furthermore, it will be appreciated that the medical device 10 can include any suitable component(s) disclosed in U.S. Patent Publication Nos. 2007/0179552, 2007/0179550, and 2007/0179581, each to Dennis et al., each filed on Jan. 30, 2006, and each of which is incorporated herein by reference in its entirety.

As shown in FIG. 1, the pacemaker device 12 can include a generator 18 (e.g., a pulse generator) and a lead 20 (e.g., a pacing lead). The lead 20 can include a proximal end 22 and a distal end 24. The lead 20 can be flexible and can include an electrically conductive material (e.g., one or more wires) for transmitting electrical signals. As shown in FIG. 2, the distal end 24 of the lead 20 can be operatively (i.e., electrically and mechanically) coupled to cardiac tissue 26 of a patient 14, and the proximal end 22 of the lead 20 can be operatively (i.e., electrically and mechanically) coupled to the generator 18. Thus, the generator 18 can receive signals via the lead 20 relating to the natural heart beat of the patient 14, and the generator 18 can transmit controlled electrical signals via the lead 20 to the cardiac tissue 26 such that the cardiac tissue 26 maintains a predetermined heart beat. It will be appreciated that the lead 20 can be electrically connected to any other biological tissue, such as a neural tissue, without departing from the scope of the present disclosure.

Also, the generator 18 can be implanted within a blood vessel 16 of the patient 14, and the lead 20 can extend through the blood vessel 16 to the cardiac tissue 26. The shape and compact nature of the generator 18 allows the generator 18 to be implanted within the blood vessel 16. In other embodiments, the generator 18 can be implanted subcutaneously, outside the blood vessel 16, and the lead 20 can extend into the blood vessel 16 to operatively couple to the cardiac tissue 26. It will be appreciated that the pacemaker device 12 can be implanted in any suitable location and be exposed to any suitable biological tissue (e.g., blood, blood vessel, fatty tissue, etc.) of the patient 14. As will be discussed in greater detail, the pacemaker device 12 can be relatively small, compact, inconspicuous, and yet, the device 12 can have a relatively long operating life.

As shown in FIG. 1, the generator 18 can generally include a control assembly 28, an energy storage device 29, and a lead connector 35. The energy storage device 29 can supply power to the control assembly 28 as will be discussed in greater detail below. The lead connector 35 can operatively couple the lead 20 to the control assembly 28 to transmit electrical signals between the cardiac tissue 26 and the control assembly 28.

The control assembly 28, energy storage device 29, and lead connector 35 can be disposed end-to-end with the control assembly 28 arranged between the energy storage device 29 and the lead connector 35. As such, the lead connector 35, the control assembly 28, and the energy storage device 29 can extend along different portions of a common, major axis X. Also, the control assembly 28, the energy storage device 29, and the lead connector 35 can each be cylindrical in shape and centered about the axis X. As shown in FIG. 1, the control assembly 28, the energy storage device 29, and the lead connector 35 can have a substantially constant width W along substantially the entire axis X of the generator 18. The generator 18 can be relatively small to facilitate implantation within the patient 14. For instance, in some embodiments, the generator 18 can have a volume of about 1.5 cubic centimeters (cc).

The energy storage device 29 can be of any suitable type, such as a battery assembly 30. As shown in FIG. 3, the battery assembly 30 can generally include an anode 36, a cathode 38, a current collector 39, a separator 40, an insulator disk 27, an insulator layer 31, and other internal components. The anode 36 can be hollow and cylindrical and can enclose the cathode 38. The cathode 38 can be solid and cylindrical. The current collector 39 can be partially embedded within and can partially extend out of the cathode 38. The separator 40 can be hollow and tubular and can be disposed between the anode 36 and the cathode 38. The insulator disk 27 and the insulator layer 31 can provide electrical insulation as will be discussed in greater detail. It will be appreciated that the battery assembly 30 can also contain an electrolyte (not specifically shown), such as a liquid electrolyte, for facilitating ionic transport and forming a conductive pathway between the anode 36 and the cathode 38.

The battery assembly 30 can also include a housing assembly 41 that encloses and substantially hermetically seals the anode 36, cathode 38, current collector 39, and separator 40. The housing assembly 41 can include an outer battery case 42 and a header assembly 44.

Figure 4:
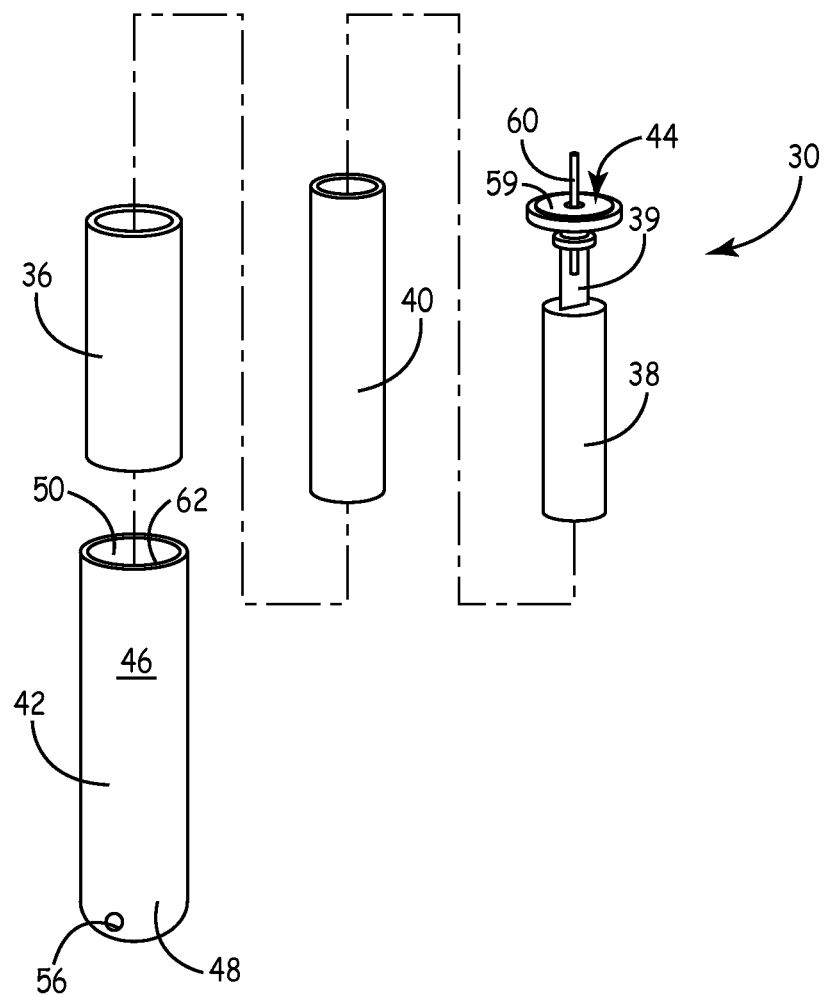
FIG. 4 is an exploded view of a battery assembly of the medical device of FIG. 1.

The battery case 42 can be hollow and cylindrical and can include an outer surface 46. The outer surface 46 can be circular, elliptical, ovate, or any other suitable shape in a cross section taken perpendicular to the axis X. Furthermore, the battery case 42 can include a closed end 48 that is rounded outward (FIGS. 3 and 4). The battery case 42 can also include an open end 50 through which the axis X extends. The battery case 42 can be made out of any suitable material, such as titanium. It will be appreciated that the battery case 42 can be the outermost surface of the battery assembly 30 so that patient 14 is directly exposed to (in direct contact with) the battery case 42. As such, the battery case 42 is not covered by any covering layer so that the patient 14 is directly exposed to the battery case 42.

Figure 16:
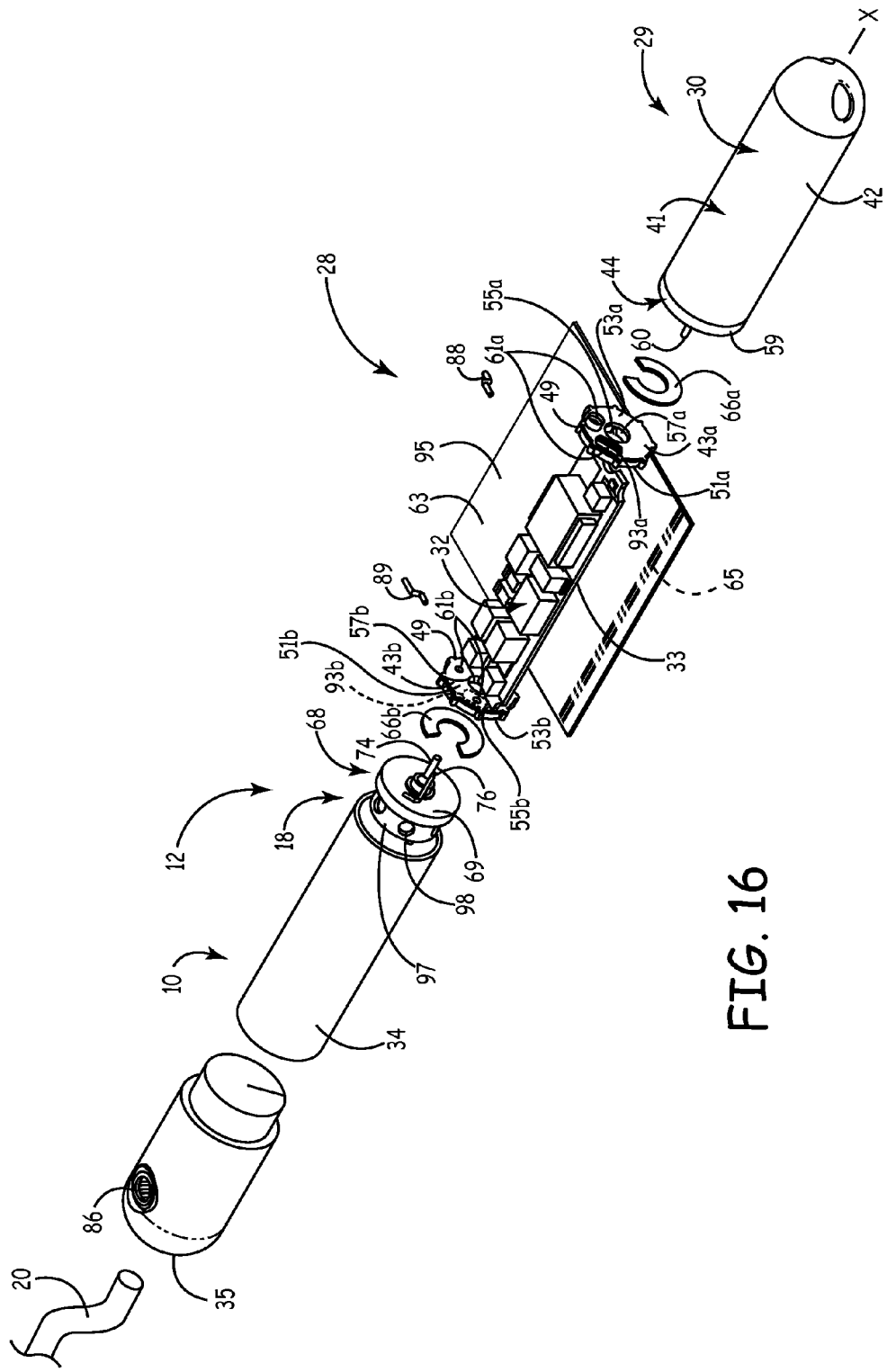
FIG. 16 is an exploded view of the medical device of FIG. 1.

Also, as shown in FIG. 3, the header assembly 44 can include a cover 59. The cover 59 can be thin and disc-shaped. The cover 59 can cover the open end 50 of the battery case 42 and can hermetically seal the open end 50. For instance, the cover 59 can be welded (e.g., via laser welding) to the open end 50 of the battery case 42. The header assembly 44 can also include a pin 60 (i.e., first electrode). The pin 60 can be substantially axially straight and can be centered on the axis X. The pin 60 can be electrically connected to the current collector 39 within the battery case 42 and can extend through the cover 59 to an area outside the battery case 42 (FIGS. 3 and 16). The cover 59 can be made out of any suitable material, such as an electrically-conductive material (e.g., titanium). Moreover, the insulator layer 31 can be disposed between the cover 59 and the pin 60 to provide electrical insulation between the cover 59 and the pin 60 and to substantially hermetically seal the pin 60. The insulator layer 31 can be made out of any suitable insulator, such as a glass material. The insulator disk 27 can be disposed between the current collector 39 and the cover 59 to provide electrical insulation between the cover 59 and the current collector 39. In addition, the header assembly 44 can include a fill port 64 (FIG. 3) that extends through the cover 59 in a direction substantially parallel to the axis X and spaced from the axis X. The fill port 64 can be a sealed through-hole extending through the cover 59.

To manufacture the battery assembly 30, the anode 36, cathode 38, and separator 40 can be assembled and received within the battery case 42 through the open end 50 such that the battery case 42 substantially encloses those components. Then, the header assembly 44 can be fixed to the open end 50 of the battery case 42 (e.g., by a continuous, ring-shaped welded joint that extends about the axis X). Next, electrolyte material can be introduced into the battery case 42 through the fill port 64, and then the fill port 64 can be sealed (e.g., by a weld, by a separate plug, or by both). It will be appreciated that the battery assembly 30 can be manufactured independently from other components of the pacemaker device 12. As such, manufacturing of the pacemaker device 12 can be completed in a more efficient manner.

Referring now to FIGS. 1 and 16-19, the control assembly 28 will be discussed in greater detail. As shown, the control assembly 28 can include a plurality of electrical control components, generally indicated at 32. The control components 32 can include one or more integrated circuits having one or more amplifiers, capacitors, diodes, wiring, microprocessors, memory, and the like, for processing and controlling electrical signal transmissions via the lead 20 of the pacemaker device 12. The control components 32 can be mounted to and supported by a circuit board 33 (FIGS. 16-19).

Figure 17:
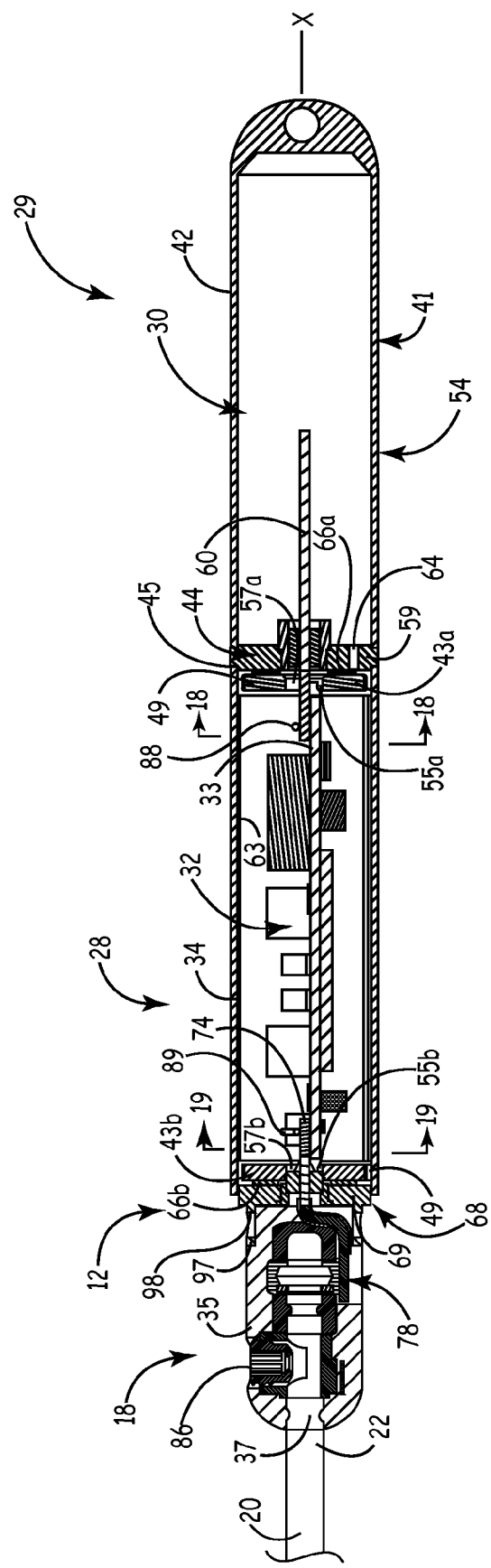
FIG. 17 is a section view of the medical device of FIG. 16.

As shown in FIGS. 16 and 17, the control assembly 28 can also include a first spacer 43a and a second spacer 43b. The first and second spacers 43a, 43b can be substantially identical and can be flat, round discs with a plurality of projections 49 radiating outward therefrom. The first and second spacers 43a, 43b can also each include a respective inner face 51a, 51b and a respective outer face 53a, 53b. The first and second spacers 43a, 43b can be disposed on opposite ends of the circuit board 33 such that the respective inner faces 51a, 51b face the circuit board and such that the spacers 43a, 43b are centered about the axis X. Also, the inner faces 51a, 51b can each include a rectangular inner recess 55a, 55b that receives the respective end of the circuit board 33. In some exemplary embodiments, the inner recess can be approximately 0.005 inches deep. It will be appreciated that the recesses 55a, 55b can ensure proper orientation of the spacers 43a, 43b with respect to the circuit board 33, and the recesses 55a, 55b can allow the control assembly 28 to be more compact.

Furthermore, the spacers 43a, 43b can each include a respective central opening 57a, 57b. The openings 57a, 57b can be centered along the axis. The spacers 43a, 43b can each further include one or more respective lead openings 61a, 61b (FIG. 16). The lead openings 61a, 61b can extend parallel to the axis X and can be disposed on a single side of the circuit board 33. Additionally, the spacers 43a, 43b can each include respective recesses 93a, 93b (FIG. 16) on the respective outer face 53a, 53b thereof. The recesses 93a, 93b can be oblong and can be disposed over the respective lead openings 61a, 61b.

Moreover, the control assembly 28 can include an insulator sheet 63. As shown in FIG. 16, the insulator sheet 63 can be a flat, rectangular, thin sheet of material. The insulator sheet 63 can be made out of any suitable electrically insulating material, such as polyimide. As shown in FIG. 17, the insulator sheet 63 can be wrapped in a tube to enclose the control components 32 and the circuit board 33, between the spacers 43a, 43b. For instance, the insulator sheet 63 can include a strip of pressure sensitive adhesive 65 (FIG. 16) that extends along one edge substantially parallel to the axis X. The opposite edge 95 (FIG. 16) can be wrapped around the control components 32 and the circuit board 33 to affix to the adhesive 65. As such, the insulator sheet 63 can provide electrical insulation for the control components 32 as will be discussed in greater detail below.

Additionally, the control assembly 28 can include a first adhesive tape 66a and a second adhesive tape 66b. The tapes 66a, 66b can be substantially identical, and can be in the shape of an incomplete annular ring. The first tape 66a can be adhesively affixed to the outer face 53a of the first spacer 43a, and the second tape 66b can be adhesively affixed to the outer face 53b of the second spacer 43b. The first tape 66a can be oriented about the axis X so as to cover one of the lead openings 61a of the first spacer 43a and to leave the other lead opening 61a uncovered. Likewise, the second tape 66b can be oriented about the axis X so as to cover one of the lead openings 61b of the second spacer 43b and to leave the other lead opening 61b uncovered.

Furthermore, the control assembly 28 can include an outer control housing 34 (shown in phantom in FIG. 1 and shown in solid lines in FIGS. 16 and 17). The control housing 34 can be made out of any suitable material, such as titanium or other electrically conductive material. The control housing 34 can be hollow, cylindrical, and open at both ends. The control housing 34 can at least partially enclose the control components 32, the circuit board 33, the insulator sheet 63, the spacers 43a, 43b, and the tapes 66a, 66b. The projections 49 of the spacers 43a, 43b can abut against the control housing 34 as shown in FIG. 17. As such, the spacers 43a, 43b can maintain the circuit board 33 in a substantially fixed position within the control housing 34. As will be discussed in greater detail below, the control housing 34 can be coupled to the housing assembly 41 of the energy storage device 29. For instance, the control housing 34 can be mechanically coupled to the housing assembly 41 via any suitable method (e.g., laser welding). Also, the control housing 34 can be electrically coupled to the housing assembly 41 such that the control housing 34 can be electrically charged.

It will be appreciated that the insulator sheet 63 can be disposed between control housing 34 and the control components 32 (FIG. 17) to thereby electrically insulate the housing 34 from the control components 32. Also, it will be appreciated that the control housing 34 can be the outermost surface of the control assembly 28 so that the patient 14 is directly exposed to (in direct contact with) the control housing 34. As such, the control housing 34 is not covered by any covering layer so that the patient 14 is directly exposed to the control housing 34.

The control assembly 28 can further include a connector assembly 68 (FIGS. 16 and 17). The connector assembly 68 can include a cap 69, a feed through pin 74, and a case connector 76. The cap 69 can be round, flat, and disc-shaped with a ring-shaped flange 97 (FIGS. 16 and 17). The flange 97 can include a plurality of openings 98 that are spaced about the axis X. The cap 69 can be fixed to the control housing 34 in any suitable fashion. For instance, the cap 69 can be partially received in the control housing 34, adhesively fixed to the tape 66b, and fixed to the control housing 34 (e.g., via laser welding). Moreover, the feed through pin 74 can extend from within the control housing 34, through the cap 69, to an area outside the control housing 34 as shown in FIG. 17. The feed through pin 74 can be electrically insulated from the cap 69 (e.g., via a layer of glass or other insulator between the pin 74 and cap 69). Also, the case connector 76 can be a bent, stiff wire that is electrically and mechanically connected to the cap 69 (e.g., via welding).

Figure 19:
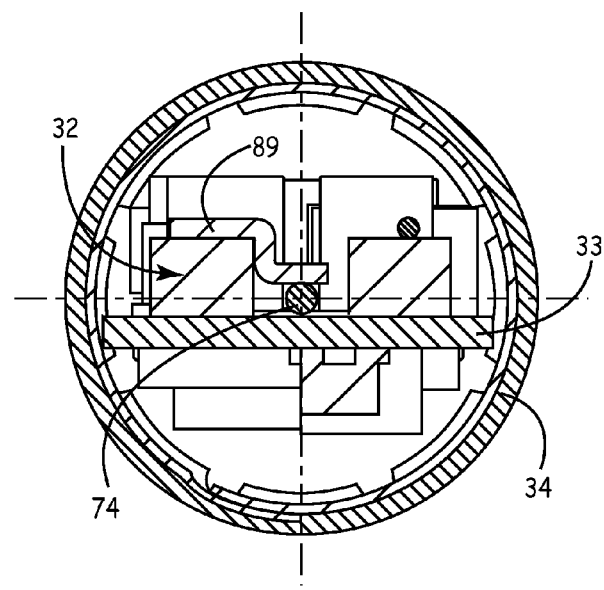
FIG. 19 is a section view of the medical device taken along the line 19-19 of FIG. 17.

When assembled, the pin 74 can extend through the tape 66b, through the central opening 57b of the spacer 43b to electrically connect to the control components 32. More specifically, as shown in FIGS. 16-17 and 19, the control assembly 28 can also include a bent wire 89 that extends generally perpendicular to the axis X. The bent wire 89 can extend between and be electrically connected to one of the control components 32 and the pin 74. As such, the pin 74 need not be bent in order to electrically connect to the control components 32. Accordingly, proper electrical connection can be ensured, and manufacturing can be facilitated.

Moreover, when the generator 18 is assembled, the case connector 76 can extend through one of the lead openings 61b in the spacer 43b to electrically connect to one of the control components 32. As will be discussed, the case connector 76 can have an opposite electrical charge than the pin 74. For instance, the case connector 76 can have a negative electrical charge, and the pin 74 can have a positive electrical charge.

Furthermore, when the generator 18 is assembled, the recess 93b can receive a portion of the case connector 76. More specifically, a weldment (not specifically shown) connecting the case connector 76 to the cap 69 can be received within the recess 93. As such, the generator 18 can be more compact.

As stated above, the generator 18 can additionally include a lead connector 35 (FIGS. 1, 16, and 17) for operably coupling the lead 20 to the generator 18. The lead connector 35 can be cylindrical and can be made out of any suitable material, such as an electrically insulative polymeric material. The lead connector 35 can include an opening 37 (FIG. 17) and an electrically conductive wire 78 embedded therein. The lead connector 35 can further include a fastener 86, such as a set screw.

The lead connector 35 can be received within the flange 97 and can be fixed to the cap 69 (e.g., via adhesives, via sonic welding, and the like). When connected, the wire 78 within the lead connector 35 can be electrically connected to the pin 74 of the control assembly 28. Furthermore, the opening 37 of the lead connector 35 can receive the proximal end 22 of the lead 20, and the fastener 86 can fixedly secure the lead 20 to the lead connector 35. When fixed to the lead connector 35, the lead 20 can be electrically connected to the wire 78.

Moreover, adhesive (not shown) can be used to fill any empty space within the lead connector 35 for more robust connection.

Figure 18:
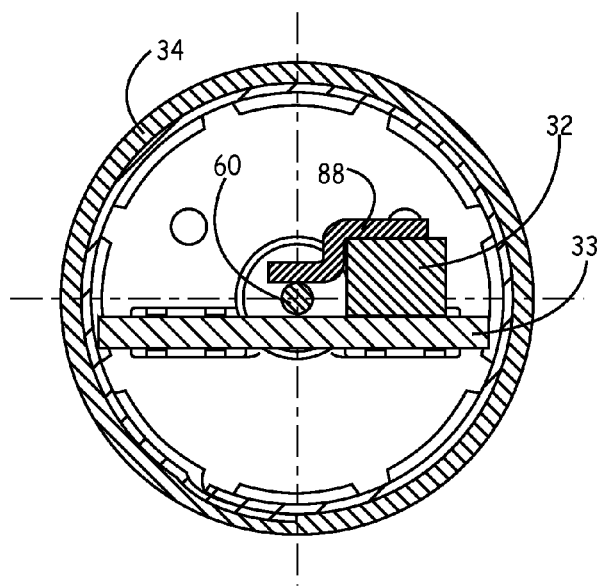
FIG. 18 is a section view of the medical device taken along the line 18-18 of FIG. 17.

In addition, the housing assembly 41 of the battery assembly 30 can be fixedly coupled and substantially hermetically sealed to the control housing 34 in any suitable fashion. In some exemplary embodiments, the cover 59 of the battery assembly 30 can be affixed to the adhesive tape 66a of the control assembly 28, and the control housing 34 can be welded to the cover 59 and the battery case 42 (e.g., via laser welding) to produce a continuous, ring-shaped weldment 45 (FIGS. 1 and 17). Also, the pin 60 of the battery assembly 30 can extend into the control housing 34, through the tape 66a, and through the central opening 55a of the spacer 43a to electrically connect to the control components 32. More specifically, as shown in FIGS. 16-18, the control assembly 28 can include a bent wire 88 that extends generally perpendicular to the axis X. The bent wire 88 can extend between and be electrically connected to one of the control components 32 and the pin 60. As such, the pin 60 need not be bent in order to electrically connect the battery assembly 30 to the control components 32. Accordingly, proper electrical connection can be ensured, and manufacturing can be facilitated.

Thus, during operation, the pin 60 of the battery assembly 30 can supply power to the control components 32 of the control assembly 28, and the control components 32 can be grounded to the control housing 34 and the battery case 42 via the case connector 76. Also, the control components 32 can supply a signal (e.g., a cardiac pacing signal) to the cardiac tissue 26 via the pin 74, the wire 78, and the lead 20, and the outer control housing 34 and the battery case 42 can be grounded to complete the circuit. This configuration can be employed if the pacemaker device 12 is a unipolar type because the control housing 34 and battery case 42 can be one pole, and the distal end 24 of the lead 20 can be the antipole. Thus, it will be appreciated that the control housing 34, the cover 59, and the cap 69 (collectively, an outer housing assembly 54 of the generator 18) can be electrically charged and act as an electrode for transmitting electrical signals between the generator 18 and the cardiac tissue 26. As such, a housing and/or insulation on the exterior of the generator 18 may not be necessary, and the generator 18 can be very compact and yet still have a high energy density. Also, manufacturing costs and manufacturing time can be reduced because fewer parts are included in the generator 18.

However, it will be appreciated that the control housing 34 and the battery case 42 can be covered externally by an insulator or another component without departing from the scope of the present disclosure. For instance, the pacemaker device 12 can be employed in a bi-polar type of pacemaker device 12, wherein the lead 20 includes coaxial conductors (not specifically shown), and the pacing signal flows between the two conductors via the cardiac tissue 26. In this exemplary embodiment, the control housing 34 and battery case 42 can be covered externally by an electrical insulator (not specifically shown). For instance, the control housing 34 and the battery case 42 can be coated with a thin layer of parylene (e.g., approximately 0.005-0.010 inches thick). As such, the control housing 34 and the battery case 42 can be visually exposed to the biological tissue of the patent (i.e., form the external surface of the generator 18), and the insulated coating can ensure proper function of the generator 18. Also, in this exemplary embodiment, the generator 18 can be very compact, and yet still have a high energy density.

Referring now to FIGS. 1, 3, 4, and 5, the cathode 38 and the anode 36 of the battery assembly 30 will be discussed in greater detail. As shown, the anode 36 can be hollow and cylindrical, and the cathode 38 can be cylindrical with a substantially solid cross-section. The respective cross section of the anode 36 and cathode 38 can be circular, elliptical, ovate, etc. The shapes of the anode 36 and cathode 38 can be adapted according to the shape of the battery case 42. Furthermore, the cathode 38 can be enclosed by and received within the anode 36. The separator 40 can also be hollow and cylindrical, and the separator 40 can be disposed between the anode 36 and cathode 38. Accordingly, the anode 36, the cathode 38, and the separator 40 can be substantially coaxial and centered along the axis X.

The anode 36, cathode 38, and separator 40 can each be made out of any suitable material. For instance, the anode 36 can include lithium, and the cathode 38 can include a hybrid mixture of carbon monofluoride ($CF_x$) and silver vanadium oxide (CSVO). Moreover, the separator 40 can include porous polypropylene film, such as commercially available Celgard 2500, Celgard 4560, and the like from Celgard, LLC of Charlotte, N.C.

As shown in FIGS. 3 and 4, the anode 36 can abut an inner surface 62 of the battery case 42. More specifically, the outer radial surface of the anode 36 extending substantially parallel to the axis X can abut the inner surface 62 of the battery case 42. As such, the battery case 42 can be in electrical communication with the anode 36.

It will be appreciated that the pin 60 can have a positive electrical charge, and the battery case 42 can have a negative electrical charge. Also, the battery case 42 can be exposed to and in direct electrical connection with tissue or other biological material of the patient 14. For instance, the outer surface 46 of the battery case 42 can abut tissue or other biological material of the patient 14. As such, the battery assembly 30 and the generator 18 can be substantially compact, making the pacemaker device 12 more comfortable to wear and more inconspicuous, and yet the battery assembly 30 can still provide adequate power over a long period of time.

For instance, if the battery assembly 30 provides about 2.5 volts, 0.15 ms pacing, 100% pacing, 60 bpm, and 825 ohm lead impedance, the expected operating life of the battery assembly 30 can be about 5.8 years. Furthermore, if the battery assembly 30 provides about 2.5 volts, 0.24 ms pacing, 100% pacing, 70 bpm, and 578 ohm lead impedance, the expected operating life of the battery assembly 30 can be about 4.8 years. Moreover, if the battery assembly 30 provides about 2.5 volts, 0.60 ms pacing, 100% pacing, 80 bpm, and 440 ohm lead impedance, the expected operating life of the battery assembly 30 can be about 2.7 years.

The battery assembly 30 can have a relatively high energy density (i.e., energy capacity/volume). For instance, in some embodiments, the battery assembly 30 can have an energy density of at least about 0.09 Ampere-hours/cubic centimeters (Ah/cc). Furthermore, the battery assembly 30 can have an energy density of between about 0.10 Ah/cc and 0.40 Ah/cc. Furthermore, the battery assembly 30 can have a capacity of about 190 mAh and a volume of about 0.63 cc for an energy density of about 0.30 Ah/cc.

Moreover, in some embodiments, the battery assembly 30 can have diameter from about 2 mm to 7.5 mm and a length from about 8 mm to 90 mm. The electrode area of the battery assembly 30 can be from about 0.137 $cm^2$ to 12.0 $cm^2$. Furthermore, the battery assembly 30 can have an energy capacity from about 0.003 Ah to 1.589 Ah. Accordingly, the battery assembly 30 provides a relatively high energy capacity.

Additionally, as shown in FIGS. 1 and 3, the housing assembly 54 can include an aperture 56, such as a through-hole that extends along an axis $X_1$ (FIG. 3). Moreover, the axis $X_1$ of the aperture 56 can be substantially centered on the axis X so as to intersect the axis X. Also, the axis $X_1$ of the aperture 56 can be substantially perpendicular to the axis X of the housing assembly 54. Moreover, the aperture 56 can be included adjacent the closed end 48 of the battery case 42 such that the battery assembly 30 is disposed between the aperture 56 and the control assembly 28. It will be appreciated that the aperture 56 could be defined in any region of the housing assembly 54 and that the aperture 56 could be of any suitable type other than a through-hole.

The aperture 56 can enable the housing assembly 54 to be coupled to the patient 14. For instance, as shown in FIG. 1, a suture 58 can extend through the aperture 56, and the suture 58 can be mechanically coupled to anatomical tissue of the patient 14. The suture 58 can be of any suitable type. As discussed above, the generator 18 of the pacemaker device 12 can be implanted within a blood vessel 16 of the patient 14. The suture 58 can couple the generator 18 to the wall of the blood vessel 16. In other embodiments, the suture 58 can extend out of the blood vessel 16 and attach to connective tissue (not shown) outside the blood vessel 16. As such, the generator 18 is unlikely to move downstream with the flow of blood through the blood vessel 16 or into an organ located downstream (e.g., the lungs). Accordingly, the aperture 56 allows the generator 18 to be secured to the patient 14 in a convenient, secure, safe, and compact fashion.

In addition, the suture 58 can facilitate handling of the generator 18. For instance, when the generator 18 needs to be removed from the patient 14 (e.g., when the battery assembly 30 needs to be replaced), the suture 58 can be grabbed onto (e.g., with a gripping tool) to pull the generator 18 from the blood vessel 16.

Referring now to FIGS. 6 and 7, an alternative exemplary embodiment of the battery assembly 130 is illustrated. Components that are similar to the embodiments of FIGS. 1-5 are indicated with corresponding reference numerals increased by 100.

As shown in FIGS. 6 and 7, the cathode 138 can be hollow and substantially cylindrical. In addition, the anode 136 can be substantially cylindrical and received within the cathode 138. Also, the separator 140 can be included between the anode 136 and the cathode 138. The cathode 138 can abut the inner surface 162 of the battery case so as to electrically couple the cathode 138 and the battery case 142. Also, the battery assembly 130 can include a connector 170 that electrically connects the anode 136 to the pin 160 of the header assembly 144. The connector 170 can be substantially flat and elongate and can be made out of a flexible material.

It will be appreciated that the pin 160 can have a negative electrical charge because it is electrically connected of the anode 136, and the battery case 142 can have a positive electrical charge because it is electrically connected to the cathode 138. The battery case 142 can be electrically coupled to tissue of the patient 14, or the battery case 142 can be electrically coupled to the control components 32 of the control assembly 28 in any suitable manner. Also, the pin 160 can be grounded to any suitable ground.

Furthermore, it will be appreciated that, over the operating lifetime of the battery assembly 130, the cathode 138 can increase in size. Because the cathode 138 is in abutment with the inner surface 162 of the battery case 142, such increase in size of the cathode 138 can cause increased abutment between the cathode 138 and the inner surface 162 of the battery case 142. Accordingly, electrical connection between the cathode 138 and the battery case 142 is ensured over the operating life of the battery assembly 130.

Moreover, it will be appreciated that, as the battery assembly 130 discharges energy, the anode 136 can decrease in size.

However, the connector 170 can be thin and flexible so as to maintain connection between the anode and the header assembly 144, even if the anode 136 decreases in size.

Figure 8:
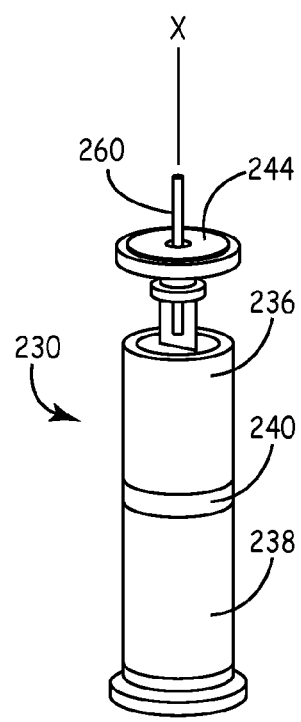
FIG. 8 is a perspective view of a portion of another exemplary embodiment of the battery assembly of the medical device.

Referring now to FIG. 8, another exemplary embodiment of the battery assembly 230 is illustrated. Components similar to the embodiments of FIGS. 1-5 are indicated with corresponding reference numerals increased by 200.

As shown, the anode 236 can be substantially cylindrical with a solid cross-section. Likewise, the cathode 238 can be substantially cylindrical with a substantially solid cross-section. Both the anode 236 and the cathode 238 can be coaxial and centered along the axis X. Furthermore, the cathode and the anode 238, 236 can be disposed in spaced relationship in a direction substantially parallel to the axis X. The separator 240 can be substantially flat and circular and disposed between the anode 236 and the cathode 238. The battery assembly 230 can also include an additional separator (not shown), for instance, between anode 236 and the battery case.

The anode 236 can be connected electrically to the pin 260, and the cathode 238 can abut the inner surface of the battery case, as discussed above. Accordingly, the battery assembly 230 can be relatively compact and yet provide sufficiently high energy density, as discussed above. Furthermore, in some embodiments, the cathode 238 can be electrically connected to the pin 260, and the anode 236 can be electrically connected to the battery case without departing from the scope of the present disclosure.

In some embodiments, the battery assembly 230 can have diameter from about 2 mm to 7.5 mm and a length from about 8 mm to 90 mm. The electrode area of the battery assembly 230 can be from about 0.011 $cm^2$ to 0.356 $cm^2$. Furthermore, the battery assembly 230 can have an energy capacity from about 0.005 Ah to 1.6 Ah. Accordingly, the battery assembly 230 provides a relatively high energy capacity.

Figure 9:
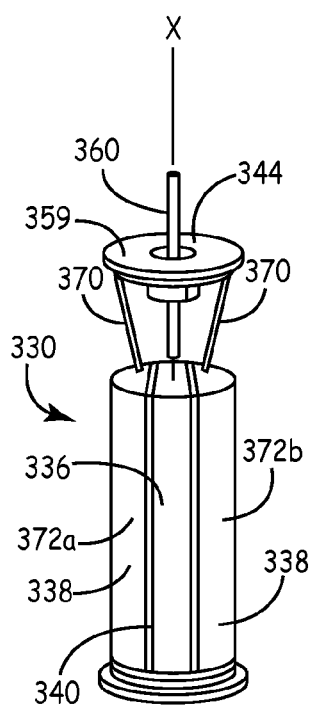
FIG. 9 is a perspective view of a portion of another exemplary embodiment of the battery assembly of the medical device.
Figure 5:
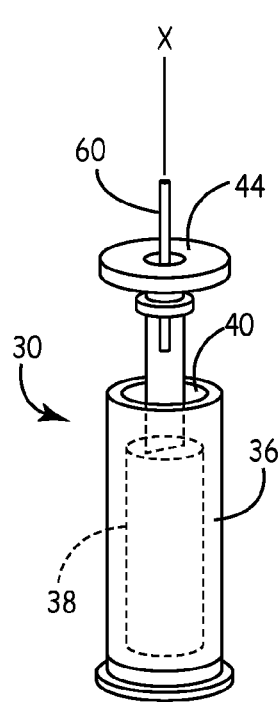
FIG. 5 is a perspective view of a portion of the battery assembly of FIG. 4.

Referring now to FIG. 9, another exemplary embodiment of the battery assembly 330 is illustrated. Components that are similar to the embodiments of FIGS. 1-5 are indicated with corresponding reference numerals increased by 300.

As shown, the cathode 338 can include a first portion 372a and a second portion 372b. Each of the portions 372a, 372b can be elongate and can have a substantially D-shaped cross-section. Furthermore, the first and second portions 372a, 372b can be disposed on opposite sides of the axis X and spaced away from each other in a direction perpendicular to the axis X. The anode 336 can be elongate and can have a rectangular cross-section. Also, the anode 336 can be substantially centered on the axis X. The anode 336 can be disposed between the first and second portions 372a, 372b of the cathode 338. More specifically, the anode 336 is disposed adjacent the respective flat portions of the first and second portions 372a, 372b. The separator 340 can be disposed between the anode 336 and the first and second portions 372a, 372b of the cathode 338.

The anode 336 can be electrically coupled to the pin 360 as discussed above. Furthermore, as shown in FIG. 9, respective connectors 370 can electrically couple one of the first and second portions 372a, 372b to the cover 359 of the header assembly 344. In addition, the pin 360 can be electrically insulated from the cover 359. It will be appreciated that the connectors 370 can be substantially flexible such that, as the first and second portions 372a, 372b of the cathode change in size during operation, the connectors 370 can flex to maintain a proper electrical connection between the respective portion 372a, 372b and the cover 359.

In the embodiment of FIGS. 10 and 11, the configuration of the anode 336' and the cathode 338' is substantially similar to the configuration of FIG. 9. However, the connectors 370' are configured differently. For instance, connectors 370' can extend from each of the first and second portions 372a', 372b' and electrically connect to the pin 360' such that the pin 360' has a positive electrical charge. In addition, a connector 370' can extend from an opposite end of the anode 336' and electrically connect to the battery case 342' such that the battery case 342' has a negative electrical charge. It will be appreciated that the connectors 370' can be flexible so as to maintain electrical connection despite changes in size of the anode 336' and/or cathode 338'.

In some embodiments, the battery assembly 330, 330' can have diameter from about 2 mm to 7.5 mm and a length from about 8 mm to 90 mm. The electrode area of the battery assembly 330, 330' can be from about 0.091 $cm^2$ to 8.0 $cm^2$. Furthermore, the battery assembly 330, 330' can have an energy capacity from about 0.103 Ah to 0.4 Ah. Accordingly, the battery assembly 330, 330' provides a relatively high energy capacity.

Referring now to FIGS. 12 and 13, another exemplary embodiment of the battery assembly 430 is illustrated. Components that are similar to the embodiments of FIGS. 1-5 are indicated with corresponding reference numerals increased by 400.

As shown, the anode 436 can include a first portion 480a and a second portion 480b. The first and second portions 480a, 480b can be substantially elongate and can have a D-shaped cross-section (FIG. 13). Also, the first and second portions 480a, 480b can be disposed on opposite sides of the axis X. In addition, the cathode 438 can have a substantially rectangular cross-section and can be disposed between the first and second portions 480a, 480b of the anode 436.

In addition, connectors can electrically couple the first and second portions 480a, 480b and the cover 459 of the header assembly 444. Also, a connector can electrically couple the cathode 438 and the pin 460 of the header assembly 444. Furthermore, the pin 460 can be electrically insulated from the cover 459 of the header assembly 444. As discussed above, the connectors 470 can be flexible to accommodate any change in size of the anode 436 and/or cathode 438.

Referring now to FIGS. 14 and 15, another exemplary embodiment of the battery assembly 530 is illustrated. Components that are similar to the embodiments of FIGS. 1-5 are indicated with corresponding reference numerals increased by 500.

As shown, the anode 536 and the cathode 538 can be both substantially D-shaped in cross-section (FIG. 15), and the anode and cathode 536, 538 can be both elongate. More specifically, the anode 536 can define a flat portion 582, and the cathode 538 can includes a flat portion 581. The flat portions 582, 581 substantially face each other. Also, both the anode 536 and the cathode 538 can include a rounded portion 584, 583, respectively. The rounded portions 584, 583 can face the inner surface 562 of the battery case 542. Also, the separator 540 can be thin and elongate and can be disposed between the anode 536 and the cathode 538.

Furthermore, as shown in FIG. 14, the battery assembly 530 can include a plurality of connectors 570. For instance, a connector 570 can extend between the anode 536 and the cover 559 of the header assembly 544. Likewise, a connector 570 can extend between the cathode 538 and the pin 560. It will be appreciated that the connectors 570 can be flexible to accommodate any change in size of the anode 536 and/or the cathode 538. Furthermore, it will be appreciated that a connector 570 could electrically connect the cathode 538 and the cover 559 while a different connector 570 could electrically connect the anode 536 and the pin 560 without departing from the scope of the present disclosure.

Figure 20:
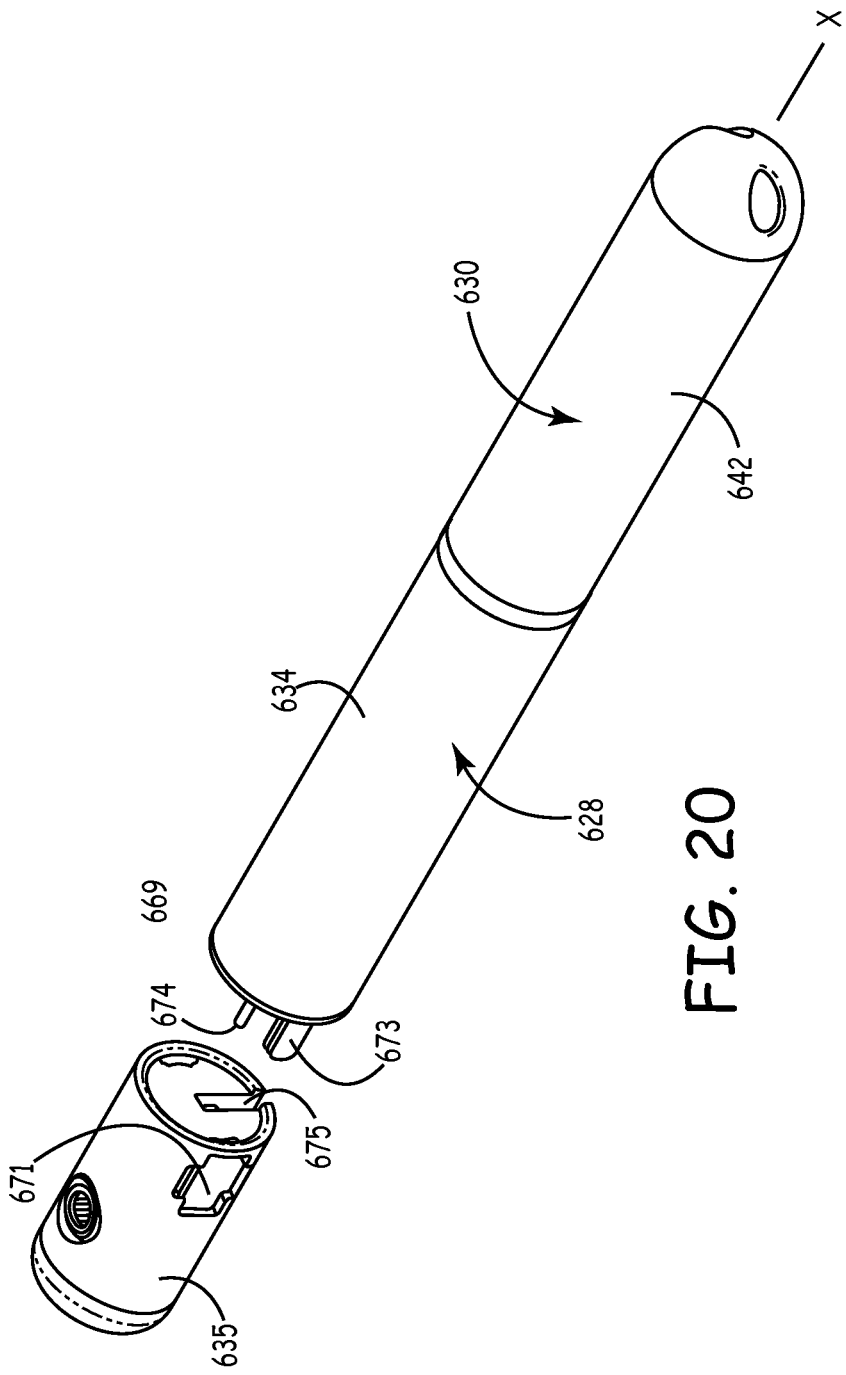
FIG. 20 is an exploded view of the medical device according to various other exemplary embodiments of the present disclosure.
Figure 21:
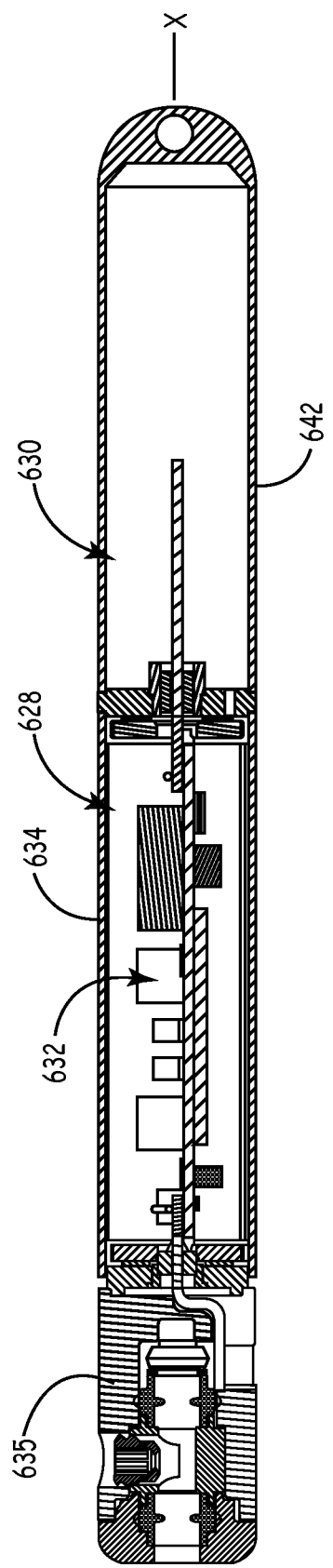
FIG. 21 is a section view of the medical device of FIG. 20.

Referring now to FIGS. 20 and 21, another exemplary embodiment is illustrated. Components that are similar to the embodiments of FIGS. 1-5 and 16-19 are indicated by similar reference numerals increased by 600.

As shown, the lead connector 635 can be substantially similar to the lead connector 35 of the embodiments shown in FIGS. 16 and 17. However, the lead connector 635 can include one or more conductive members 671 (FIG. 20). In some embodiments, there are a plurality of conductive members 671 spaced apart about the axis X. The conductive member(s) 671 can be made out of any suitable electrically conductive material, such as titanium. The conductive member(s) 671 can be embedded within surrounding polymeric material of the lead connector 635.

Moreover, the cap 669 of the control assembly 628 can include a projection 673 extending toward the lead connector 635. The projection 673 can be made out of electrically conductive material and can be integrally connected to other portions of the cap 669 so as to be monolithic. The projection 673 can be received within a slot 675 of the lead connector 635, and the projection 673 can electrically connect with the conductive member(s) 671 inside the lead connector 635.

In some exemplary embodiments, the lead connector 635 can be coupled to the control assembly 628 via welding. For instance, the lead connector 635 can be joined via a laser spot welding process, wherein the conductive member(s) 671 serve as an electrical contact for the welding process, and the control housing 634 or the battery case 642 serves as another electrical contact for the welding process. Accordingly, it will be appreciated that the lead connector 635 can be fixedly coupled to the control housing 634 in a very robust manner.

Thus, in summary, each of the exemplary embodiments of the implantable medical device 10 can be substantially compact, while still having a sufficient operating life. As such, the generator 18 can be implanted inconspicuously and comfortably within the patient 14, and yet the generator 18 can operate for an extended period of time before repair and/or replacement of the generator 18 becomes necessary.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Exemplary embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A battery assembly for a medical device, the battery assembly comprising:
   a cathode consisting of a single, solid, cylindrical elongate cathode comprising a mixture of carbon monofluoride and silver vanadium oxide, the cathode having first and second ends opposite one another and parallel one another;
   a current collector within the cathode; an anode consisting of a single, tubular-shaped lithium metal anode;
   a separator consisting of a single, tubular-shaped separator disposed between the anode and the cathode and having a closed end covering the second end of the cathode, the cathode, anode and separator being coaxial;

an electrolyte;

a cylindrical housing assembly electrically coupled to the anode and encapsulating the cathode, the anode, the separator and the electrolyte, the housing having a fillport; and a feedthrough pin exposed from and electrically insulated from the housing assembly, the cathode being electrically coupled to the feedthrough pin through the current collector within the cathode.

2. The battery assembly of claim 1, wherein the housing assembly is made from titanium.

3. The battery assembly of claim 1, wherein the feedthrough pin is electrically insulated from the housing assembly with an insulator made from a glass material.

4. The battery assembly of claim 1, wherein the housing assembly includes a battery case and a cover, wherein the feedthrough pin extends through the cover, a glass material disposed between the first electrode and the cover, the glass material forming a hermetic seal between the first electrode and the cover.

5. The battery assembly of claim 4 further comprising an insulator disk disposed between the current collector and the cover.

6. The battery assembly of claim 1 wherein the separator comprises porous polypropylene.

7. The battery assembly of claim 1 wherein the housing assembly includes a suture through-hole at a distal end of the housing assembly.

8. The battery assembly of claim 1 wherein the housing assembly includes a battery case and a cover and the fillport is in the cover.

9. The battery assembly of claim 1 wherein the current collector has a rectangular shape.

10. The battery assembly of claim 1 wherein the current collector has two major surfaces opposite one another and parallel one another.

* * * * *